United States Patent
Anderson et al.

(10) Patent No.: US 6,521,668 B2
(45) Date of Patent: *Feb. 18, 2003

(54) COSMETIC COMPOSITION AND METHODS OF USE

(75) Inventors: Glen T. Anderson, Cortlandt Manor, NY (US); Dmitri Ptchelintsev, Mahwah, NJ (US); Michael Traudt, Brookfield, CT (US)

(73) Assignee: Avon Products, Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/461,448

(22) Filed: Dec. 14, 1999

(65) Prior Publication Data

US 2002/0054891 A1 May 9, 2002

(51) Int. Cl.⁷ .............................................. A61K 31/12
(52) U.S. Cl. ...................................... 514/679; 424/401
(58) Field of Search ........................... 424/401; 514/679

(56) References Cited

U.S. PATENT DOCUMENTS

| | | |
|---|---|---|
| 4,424,234 A | 1/1984 | Anderson et al. |
| 4,603,046 A | 7/1986 | Georgalas |
| 4,742,066 A | 5/1988 | Deckner et al. |
| 5,093,109 A | 3/1992 | Mausner |
| 5,266,344 A | 11/1993 | Mimura et al. ............. 426/546 |
| 5,861,415 A | 1/1999 | Majeed et al. |
| 5,972,993 A | * 10/1999 | Ptchelintsev ................ 514/449 |

FOREIGN PATENT DOCUMENTS

| | | | |
|---|---|---|---|
| EP | 0 774 249 A2 | | 5/1997 |
| EP | 0 666 735 | | 10/1998 |
| GB | 2 259 014 | * | 3/1993 |
| JP | 3-5423 | | 1/1991 |
| JP | 6128133 | * | 5/1994 |
| WO | WO 99/55352 | * | 11/1999 |
| WO | WO 00/61162 | | 10/2000 |

OTHER PUBLICATIONS

Saija, Antonella et al., Influence of Different Penetration Enhancers on in Vitro Skin Penetration & in Vivo Photoprotective Effect of Flavonoids, 1998, 85–94.*

* cited by examiner

Primary Examiner—Jose' G. Dees
Assistant Examiner—Michael A. Williamson
(74) Attorney, Agent, or Firm—Ohlandt, Greeley, Ruggiero & Perle, LLP

(57) ABSTRACT

There are disclosed cosmetic compositions and methods for protection of keratinous tissue against environmental aggressors, such as smoke, smog and UV radiation. The compositions have as an essential antioxidant: (i) hesperetin, (ii) tetrahydrocurcumin, (iii) tetrahydrodemethoxycurcumin, or (iv) tetrahydrobisdemethoxycurcumin, or mixtures of thereof. The compositions are preferably in the form of oil in water emulsions and may optionally contain one or more emulsifiers, preservatives, thickeners, sunscreens, additional antioxidants, emollients, skin protectants, hair protectants, nail protectants and the like.

13 Claims, No Drawings

COSMETIC COMPOSITION AND METHODS OF USE

BACKGROUND OF THE INVENTION

1. Field of the Invention

The present invention relates to cosmetic, particularly skin care and treatment, compositions. More particularly, the present invention relates to emulsified cosmetic compositions having certain antioxidants. The antioxidants have been found highly effective in ameliorating or preventing damage to keratinous tissue, such as skin, hair and nails, caused by aggressive environmental substances, such as smoke and other atmospheric pollutants, as well as minimizing or relieving damage caused by ultraviolet radiation.

2. Description of the Prior Art

Skin treatment compositions are extensively described in the art. Emulsified skin treatment compositions are disclosed in U.S. Pat. No. 5,093,109 to Mausner, which issued on Mar. 3, 1992. This Patent provides an anti-aging composition comprising water, an anti-aging agent, a sunscreen, a preservative, a thickener, an antioxidant and an emulsifier. This Patent discloses only "Tenox II", a product of Eastman Chemical Products, Inc., and ascorbyl palmitate as suitable antioxidants.

U.S. Pat. No. 4,742,066 to Deckner et al., which issued on May 3, 1988, discloses a method for inhibiting the generation of free radicals in the skin. The method comprises applying a composition that may be in the form of an emulsion in which the free radical inhibitor may be ethoxyquin or "Trolox C". "Trolox C" is a product of Hoffmann-LaRoche.

U.S. Pat. No. 4,603,046 to Georgalas et al. issued on Jul. 29, 1986. This Patent discloses skin treatment compositions having enhanced ultraviolet absorbing properties in the form of oil-in-water emulsions. The essential ingredient is troxerutin and the preferred antioxidant is Tenox II, as disclosed in the Mausner Patent noted above.

U.S. Pat. No. 4,424,234 to Anderson et al., which issued on Jan. 3, 1984, discloses cosmetic formulations for application to the skin. The formulations have a hydroxy alkanoic acid as the essential ingredient and which may contain tocopherol, propyl gallate, ascorbyl palmitate, butylated hydroxy toluene or butylated hydroxy anisole as antioxidants. The compositions, which may be in the form of emulsions, are particularly useful for the treatment of dry skin.

U.S. Pat. No. 5,861,415 to Majeed et al., which issued on Jan. 19, 1999, discloses the pharmaceutical use as a bioprotectant of a mixture of curcumin, demethoxycurcumin and bis-demethoxycurcumin derived from the herb turmeric (*Curcuma longa*). The present invention uses the tetrahydrocurcumin derivatives as antioxidants in an emulsified skin treatment composition.

SUMMARY OF THE INVENTION

It is an object of the present invention to provide cosmetic compositions having certain antioxidants.

It is another object of the present invention to provide such compositions that have a number of benefits in connection with care of and prevention of damage to keratinous tissue. The compositions of this invention may be in the form of gels, lotions, serums, anhydrous sticks, oil based sprays, oil-in-water emulsions or water-in-oil emulsions.

It is a further object of the present invention to provide such compositions that are a strong defense against environmental aggressors such as smoke, smog, ozone, atmospheric pollutants, free radicals and ultraviolet radiation.

These and other objects of the present invention are achieved by a cosmetic composition comprising an essential antioxidant selected from the group consisting of:

(i) hesperetin;
(ii) tetrahydrocurcumin;
(iii) tetrahydrodemethoxycurcumin;
(iv) tetrahydrobisdemethoxycurcumin; and
(v) mixtures of (i), (ii), (iii) or (iv).

The composition may also include one or more emulsifiers, preservatives, thickeners and fragrances.

DESCRIPTION OF THE INVENTION

In accordance with the present invention, there has been discovered cosmetic compositions, preferably in the form of an oil in water emulsion. The term "cosmetic" includes skin care, hair care and nail care compositions. The composition has an essential antioxidant. The essential antioxidant is (i) hesperetin, (ii) tetrahydrocurcumin, (iii) tetrahydrodemethoxycurcumin, or (iv) tetrahydrobisdemethoxycurcumin, or mixtures of two or more of any of the aforesaid antioxidants. The composition may also include one or more emulsifiers, preservatives, and thickeners.

The compositions of the present invention will preferably contain either hesperetin, tetrahydrocurcumin, terahydrodemethoxycurcumin or terahydrobis-demethoxycurcumin, as an essential antioxidant ingredient. More preferably, the composition will contain at least two of these antioxidants. Most preferably, each of the four antioxidants will be present in the cosmetic composition. An even more preferred composition is the mixture of four essential antioxidants, and one or more emulsifiers, preservatives and thickeners in the form of an oil-in-water emulsion.

The compositions of the present invention offer a number of benefits in connection with care and prevention of damage to keratinous tissue. For example, the compositions are quickly absorbed, are not greasy or sticky, and are lightweight. The compositions are suitable for all skin, hair and nail types. They nourish and fortify the skin and improve the skin's appearance, especially dry or sun damaged skin. Also, the compositions provide climatic self-adjusting moisture. Importantly, the compositions provide strong defense against environmental aggressors such as smoke, smog, ozone, atmospheric pollutants, free radicals and ultraviolet radiation. Further, the compositions leave the skin smoother and less fragile. They help to prevent and temporarily protect chafed, cracked or windburned skin. When formulated in one preferred embodiment with one or more sunscreens, the compositions prevent tanning and sunburning, and reduce the risk of premature aging of the skin.

With respect to the essential antioxidants, hesperetin is 4-methoxy-5,7,3-trihydroxyflavone and has the structure:

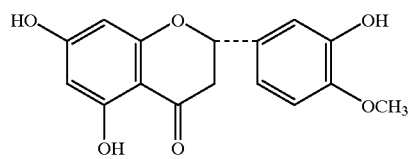

Hesperetin is used in its pure form in the present compositions, but may be isolated from grapefruit. It is also found in lemons and oranges. In the present compositions, it is present in an amount about 0.01 percentage by weight (wt. %) to about 3.0 wt. %, preferably about 0.1 wt. %, of the total weight of the composition.

Tetrahydrocurcumin, terahydrodemethoxycurcumin and terahydrobis-demethoxycurcumin may be represented by the structure:

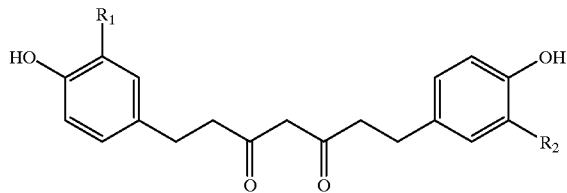

When $R_1$ and $R_2$ are $-OCH_3$, the structure represents tetrahydrocurcumin (THC). When $R_1$ and $R_2$ are, respectively, $-H$ and $-OCH_3$, the structure represents terahydrodemethoxycurcumin (THDC). When $R_1$ and $R_2$ are both $-H$, the structure represents tetrahydrobis-demethoxycurcumin (THBDC). A preferred antioxidant is a mixture of these three compounds. Such a mixture will typically contain about 75 wt. % to about 95 wt. % of THC, about 8 wt. % to about 20 wt. % of THDC, and about 1 wt. % to about 10 wt. % of THBDC. The mixture, or each of these compounds individually, i.e., THC, THDC or THBDC, may be used in the present compositions in an amount about 0.1 wt. % to about 5.0 wt. %, preferably about 0.75 wt. % to about 1.5 wt. %, and more preferably about 1.0 wt. %.

The emulsifiers may be anionic, cationic, zwitterionic, amphoteric or nonionic when the composition is prepared in the form of an oil in water or water in oil emulsion. Suitable emulsifiers include polymeric acrylate emulsifiers, polyethylene glycol 20 sorbitan monolaurate (Polysorbate 20), polyethylene glycol 5 soya sterol, sorbitan tristearate, polyethylene glycol 40 stearate, sorbitan trioleate, glyceryl, monopalmitate, diethanolamine cetyl phosphate, glyceryl monopalmitate, glyceryl monostearate, polyethylene glycol 100 stearate, cetearyl glucoside, polyethylene glycol 20 stearyl ether (Brij 78, Steareth 20), polyethylene glycol ether of lauryl alcohol (Laureth 23), polysorbate 80 (Tween 80) or lecithin. The composition or formulation will preferably contain a mixture of two or more of these emulsifiers or others that are approved for cosmetic use. The total amount of emulsifier will vary from about 1 wt. % to about 10 wt. % of the composition, preferably about 2.5 wt. % to about 3.0 wt. %

The preservatives are any preservative suitable for use in a topically applied cosmetic product. Such preservatives include imidazolidinyl urea, ethanol, benzyl alcohol, 2-phenoxyethanol, disodium EDTA (ethylenediamine tetraacetic acid), methyl paraben, ethyl paraben or butyl paraben. The preservative will be present in amounts effective to prevent bacteria growth. Typically, these amounts range from about 1 wt. % to about 3 wt. %.

Each composition should have at least one thickener to ensure that it has the proper viscosity when applied to the skin. Preferred thickeners are the carboxyvinyl polymers sold by the B.F. Goodrich Company under the trademark of Carbopol resins. Examples of such thickeners include, Carbopol 934, Carbopol 940, Carbopol 950, Carbopol 980, Carbopol 951 and Carbopol 981. Other thickeners or gelling agents that may be present include, but are not limited to, stearic acid, fatty alcohols, such as cetyl alcohol, stearyl alcohol, magnesium aluminum silicate, polyacrylamide/isoparaffin/laureth-7 (Seppigel), hydroxyethyl cellulose, propylene glycol monostearate, hydroxypropyl cellulose, carboxymethyl cellulose, xanthan gum, myristyl stearate, and cetyl stearate. The amount of thickener is in the range about 0.5 wt. % to about 2.5 wt. %, preferably about 0.6 wt. %.

Besides the antioxidant, emulsifier, preservative and thickener, the composition may include water. Water will typically comprise about 55 wt. % to about 90 wt. %, preferably about 58 wt. % to about 60 wt. % of the total weight of the composition. All of the other ingredients are emulsified or dispersed into the water, when the composition is prepared in the form of a oil in water emulsion, which is preferred, except where the ingredients are water soluble.

The present compositions will preferably contain one or more sunscreens or UV (ultraviolet) absorbing agents, when the composition is directed to day use. Preferably, the sunscreens will have at least one compound that absorbs in the UV-B region (wavelength 290 to 320 nanometers) and optionally one or more other compounds that absorb in the UV-A region (wavelength 320 to 400 nanometers). The total amount of UV absorbing agents included within the formulation will be about 2 wt. % to about 15 wt. %. It is preferred that the composition have about 7 wt. % to about 9 wt. % ethylhexyl-methoxycinnamate, about 3 wt. % to about 5 wt. % benzophenone-3 (oxybenzone), and about 1 wt. % to about 3 wt. % butyl methoxybenzoylmethane.

Suitable sunscreens are set forth below with their preferred concentrations in weight percent:

| SUNSCREEN | Wt. % |
| --- | --- |
| Oxybenzone | 2–10 |
| Sulisobenzone | 5–10 |
| Dioxybenzone | 1–3 |
| Methyl Anthranilate | 3–6 |
| Para Aminobenzoic Acid(PABA) | 5–15 |
| DEA Methoxycinnamate | 8–10 |
| Octocrylene | 7–10 |
| Octyl Methoxycinnamate* | 2–10 |
| Octyl Salicylate | 3–5 |
| Homomenthyl Salicylate | 4–15 |
| Octyl Dimethyl PABA | 1.4–5 |
| TEA Salicylate | 5–12 |
| Titanium Dioxide | 2–25 |
| Zinc Oxide | 2–25 |
| Butylmethoxy Dibenzoylmethane** | 0.1–5 |
| Octyl Triazone | 0.1–10 |
| Phenylbenzimidazole sulfonic acid | 1–4 |
| Terephthalydidene Dicamphor Sulfonic Acid and Salts Thereof*** | 0.1–5 |
| Ethyl PABA | 1–10 |
| 2-(2'-Hydroxy-5'-Methylphenyl) Benzotrizole**** | 0.5–10 |
| Methylene Bis-Benzotriazolyl-Tetramethylbutylphenol***** | 1–10 |
| Bis-Octoxyphenol Methoxyphenyl Triazine****** | 1–10 |

*The terms octyl methoxycinnamate and ethylhexyl metoxycinnamate are used interchangeably.
**A non-limiting example of butylmethoxy dibenzoylmethane is available from Givaudan under the tradename "PARSOL 1789".
***A non-limiting example of terephthalydidene dicamphor sulfonic acid and salts thereof is available from L'Oreal under the tradename "MEXORYL SX".
****A non-limiting example of 2-(2'-hydroxy-5'-methylphenyl) benzotrizole is available from Ciba-Geigy under the tradename "TINUVIN P">
*****A non-limiting example of methylene bis-benzotriazolyl-tetramethylbutylphenol is available from Ciba-Geigy under the tradename "TINOSORB-M".
******A non-limiting example of bis-octoxyphenol methoxyphenyl triazine is available from Ciba-Geigy under the tradename "TINOSORB-S".

In addition to the essential antioxidant, the composition of the present invention may preferably contain one or more additional antioxidants such as gamma oryzanol (a ferulic acid ester of cycloartenol), mixed tocopherols (a mixture of isomers of Vitamin E), ascorbyl monopalmitate, algae extract (a seaweed extract that has biomolecules of fuhalol and phloretol), tomato extract (a natural extract that contains lycopene), rosemary extract (*Rosmarinus officinalis*), or decarboxy carnosine hydrochloride(a pseudodipeptide). Most preferably, all of these additional antioxidants are present, each in amounts about 0.01 wt. % to about 1.0 wt. %.

The compositions of the present invention may also contain about 3 wt. % to about 7 wt. % of a humectant. Suitable humectants include propylene glycol, butylene glycol, glycerin, sorbitol, sodium 2-pyrrolidone-5-carboxylate, collagen, dibutyl phthalate, gelatin, and the 10 to 20 mol ethoyxylate or propoxylate of glucose.

Emollients may also be present in an amount about 3 wt. % to about 12 wt %. Suitable emollients or oleaginous materials include one or more of the following: mineral oil, petrolatum, glyceryl monooleate, myristyl alcohol, isopropyl palmitate, avocado oil, squalane, octyl palmitate, cocoa butter, sesame oil, propylene glycol dicaprylate/dicaprate, isopropyl myristate, diisopropyl dimerate (that is, the diester of isopropyl alcohol and dimer acid) and dimethicone. Preferred for use in the present compositions are petrolatum, also functioning as an occlusivity agent, $C_{12}$–$C_{15}$ alcohol esters of benzoic acid, and dicaprylyl maleate.

The present compositions, when used in the form of emulsions, may be prepared using techniques well known in the emulsion art. For example, first add any water soluble ingredients to the aqueous phase, heat the aqueous phase to about 50 to about 90° C., then disperse into the aqueous phase both the emulsifiers and oleaginous components with stirring. Then, allow the composition to cool to room temperature to form a stable emulsion.

The present invention is illustrated by the following example of a skin care and treatment composition:

EXAMPLE

A stable oil in water emulsion skin treatment composition was prepared composed of the following (% is by weight):

| Percent | Ingredient |
| --- | --- |
| 60% | demineralized water |
| 0.2% | disodium EDTA |
| 0.6% | Carbopol 934 |
| 0.75% | glyceryl monostearate |
| 0.95% | Steareth-2 emulsifier (propylene glycol 20 stearyl ether) |
| 0.95% | polyethylene glycol 40 stearate |
| 0.25% | stearyl alcohol |
| 1.0% | benzyl alcohol |
| 0.2% | methylparaben |
| 0.1% | hesperetin |
| 1.0% | mixture of tetrahydrocurcumin, terahydrodemethoxycurcumin and terahydrobis-demethoxycurcumin |
| q.s. | conventional antioxidants, sunscreens, humectants, emollients, odor remover, pH adjuster and masking agent |
| 100.00% | |

The compositions of the present invention provide many methods of protecting and improving the appearance of the skin. For example, the present invention also comprises a method of protecting the skin and preventing damage from the adverse effects of environmental substances that may come into contact with the skin, such as smoke, smog, ozone and other atmospheric pollutants. Further, the present invention includes a method of protecting the skin from sunburn damage, a method of neutralizing free radicals which may come into contact with the skin, and a method of protecting chafed, cracked, sunburned or windburned skin from further damage. The present invention also includes a method for the treatment, prevention or amelioration of skin changes associated with intrinsic or extrinsic aging. Each method comprises topically applying to the skin a composition of the present invention.

The present invention having been described with particular reference to the preferred forms thereof, it will be obvious that various changes and modifications may be made herein without departing from the spirit and scope of the present invention as defined in the appended claims.

What is claimed is:

1. A method of protecting skin from the adverse effects of an environmental aggressor selected from the group consisting of smoke, smog, ozone, and atmospheric pollutants, comprising:

applying to the skin a cosmetic composition having (a) an effective amount of an antioxidant, the antioxidant being hesperetin; and (b) a cosmetically acceptable carrier; and (c) optionally an additional antioxidant.

2. The method of claim 1, wherein the additional antioxidant is selected from the group consisting of gamma oryzanol, mixed tocopherols, ascorbyl monopalmitate, algae extract, tomato extract, rosemary extract, decarboxy carnosine hydrochloride, tetrahydrocurcumin, tetrahydrodemethoxycurcumin, tetrahydrobisdemethoxycurcumin, and any combinations thereof.

3. The method of claim 2, wherein the hesperetin is present from about 0.01 wt % to about 3.0 wt % based on the total weight of the composition.

4. The method of claim 2, wherein the additional antioxidant is tetrahydrocurcumin.

5. The method of claim 2, wherein the additional antioxidant is tetrahydrodemethoxycurcumin.

6. The method of claim 2, wherein the additional antioxidant is tetrahydrobisdemethoxycurcumin.

7. The method of claim 1, wherein the composition further comprises a sunscreen.

8. The method of claim 7, wherein the sunscreen is selected from the group consisting of:

ethylhexylmethoxycinnamate, benzophenone-B, butyl methoxydibenzoylmethane, and any combinations thereof.

9. The method of claim 1, wherein the cosmetic composition further has at least one emulsifier, preservative, thickener, emollient, humectant or fragrance.

10. The method of claim 1, wherein the cosmetic composition further has a preservative and an emollient.

11. The method of claim 10, wherein the cosmetic composition further has an emulsifier and a thickener.

12. The method of claim 11, wherein the cosmetic composition further has a fragrance.

13. The method of claim 12, wherein the cosmetic composition further has a humectant.

* * * * *